(12) United States Patent
Broborg

(10) Patent No.: US 8,449,661 B2
(45) Date of Patent: May 28, 2013

(54) FILTER ARRANGEMENT

(75) Inventor: Stefan Broborg, Haninge (SE)

(73) Assignee: Maquet Critical Care AB, Solna (SE)

( * ) Notice: Subject to any disclaimer, the term of this patent is extended or adjusted under 35 U.S.C. 154(b) by 1270 days.

(21) Appl. No.: 12/294,271

(22) PCT Filed: Mar. 29, 2006

(86) PCT No.: PCT/EP2006/061139
§ 371 (c)(1),
(2), (4) Date: Sep. 24, 2008

(87) PCT Pub. No.: WO2007/110112
PCT Pub. Date: Oct. 4, 2007

(65) Prior Publication Data
US 2009/0165800 A1 Jul. 2, 2009

(51) Int. Cl.
*B01D 53/02* (2006.01)
(52) U.S. Cl.
USPC ........... 96/137; 55/422; 55/496; 55/509; 96/149; 128/205.12
(58) Field of Classification Search
USPC ........... 128/205.12; 55/377, 500, DIG. 35, 55/328, 393, 422, 475, 496, 509, 319; 96/137, 96/149
See application file for complete search history.

(56) References Cited

U.S. PATENT DOCUMENTS

| | | | | |
|---|---|---|---|---|
| 3,823,532 A | * | 7/1974 | Cooper et al. | 55/357 |
| 4,309,200 A | * | 1/1982 | Heffernan | 55/341.2 |
| 4,370,153 A | * | 1/1983 | Russell et al. | 55/304 |
| 4,673,386 A | * | 6/1987 | Gordon | 604/48 |
| 5,147,428 A | | 9/1992 | Elliot | |
| 5,471,979 A | | 12/1995 | Psaros et al. | |
| 5,505,768 A | * | 4/1996 | Altadonna | 96/108 |
| 5,655,825 A | * | 8/1997 | Anoszko | 312/262 |
| 6,488,028 B1 | | 12/2002 | Lambert | |
| 7,077,134 B2 | | 7/2006 | Ahlmen | |
| 7,634,998 B1 | * | 12/2009 | Fenley | 128/201.13 |
| 2007/0062535 A1 | | 3/2007 | Psaros | |
| 2012/0227366 A1 | * | 9/2012 | Aycock | 55/422 |

* cited by examiner

Primary Examiner — Duane Smith
Assistant Examiner — Thomas McKenzie
(74) Attorney, Agent, or Firm — Schiff Hardin LLP

(57) ABSTRACT

To connect and disconnect a filter in a gas flow system, a filter unit has a filter housing wherein an adsorption/absorption filter is movably arranged. The filter housing has two tube connectors for connecting the filter unit in a gas conducting passage. The filter unit also has a shifting element which is movable from a first to at least a second position. The first position allows the filter to substantially fill the gas conducting passage in a way that forces the gas in the gas flow system to pass through the filter, whereas the second position substantially removes the filter from the gas conducting passage, allowing the gas to pass through the filter unit without passing the filter.

23 Claims, 7 Drawing Sheets

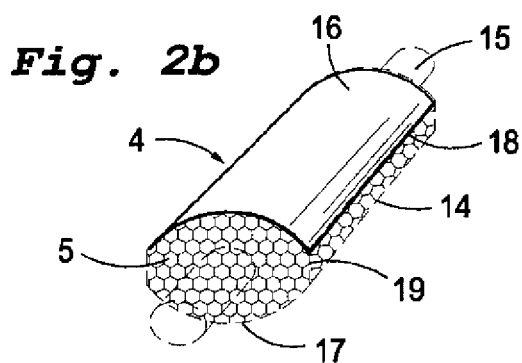
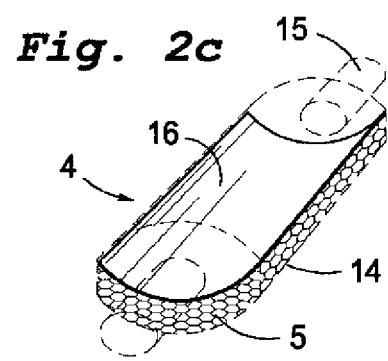
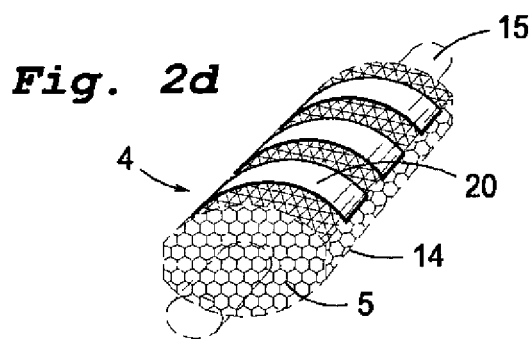
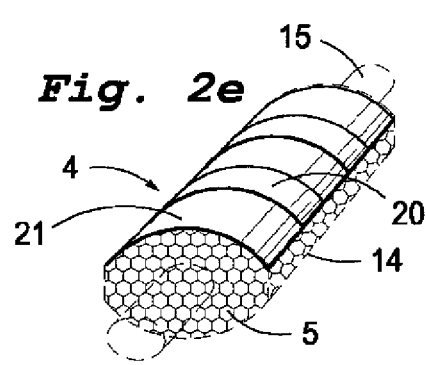
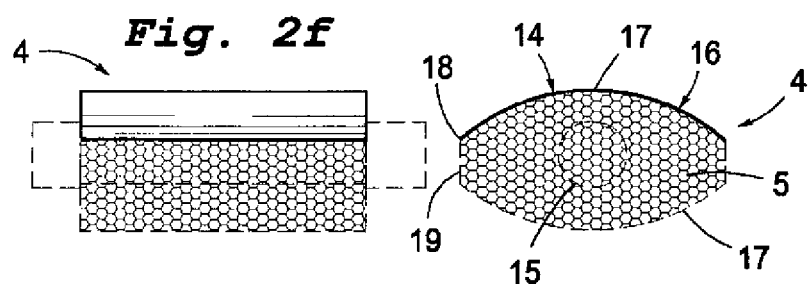
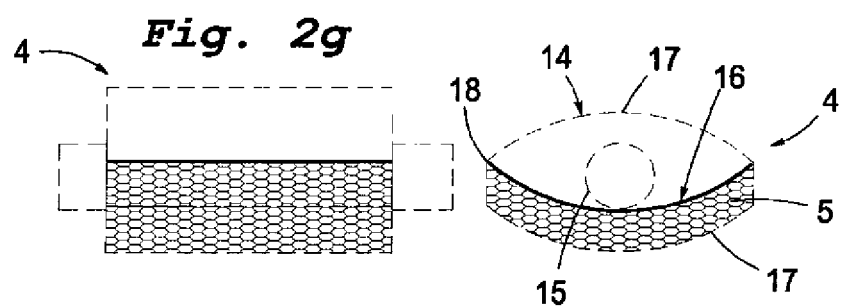

FILTER ARRANGEMENT

BACKGROUND OF THE INVENTION

1. Field of the Invention

The present invention relates to filters in gas flow systems in general and particularly to adsorption and/or absorption filters in anesthetic or sedation delivery systems.

2. Description of the Prior Art

Inhalation anesthetics are drugs that are breathed into the lungs and from there absorbed into the blood. The anesthetic blocks the perception of pain and other sensations, allowing patients to undergo surgery, sedation or other procedures without the distress and pain they would otherwise experience. To support the administration of anesthesia, anesthetic or sedation apparatus are used. In anesthetic apparatus, fresh breathing gas is mixed with highly concentrated anesthetic from an anesthetics evaporator in a conduit, leading into and out of the patient.

Some anesthetic delivery systems are particularly adapted to re-use anesthetic that is not assimilated by a patient from previously inhaled anesthetic dose. An example of such a system is disclosed in U.S. Pat. No. 5,471,979, a so called anesthesia reflector system. During exhalation, the exhalation gas passes through an adsorption and/or absorption filter wherein the anesthetic that is not assimilated by the patient is adsorbed and/or absorbed, while the majority portion of the exhalation gas passes through the filter and is evacuated from the system. During inhalation, the adsorbed/absorbed anesthetic is desorbed from the adsorption and/or absorption material in the filter, and is re-supplied to the patient. That is, the adsorption and/or absorption filter operates as a reflector of anesthetics.

When it is time to wake up the patient, or if some patient related parameter indicates that the level of anesthetic/sedation is too deep, it is desirable to cut off the supply of anesthetic quickly. This is, however, impossible in reflector anesthetic delivery systems since some medium remains in the filter. When the supply of anesthetic to the patient must be interrupted, there are mainly two alternatives depending on how urgent the patient's need for fresh breathing gas is. The first alternative is to gradually air out the anesthetic but this takes time and in the meanwhile the patient receives an undesired supply of the medium. The second alternative is to remove the entire filter unit from the respiration circuit, as is known in the Hudson Anaconda™ sedation system. The filter unit removal is accomplished manually and since the tubes attached to the filter unit must be disconnected, the gas flow circuit is broken, resulting in that some of the anesthesia agent inevitably will be discharged into the surrounding air, potentially exposing the medical personnel. It has also the drawback that an undesirable decrease in pressure in the patient's lungs can occur.

To be able to cut off the supply of anesthetic quickly, without breaking the gas flow circuit, WO 03/090826 presents an anesthetic delivery system with an advanced air-regulation system comprising several different flow sections of which one directs the inhalation gas in a manner that makes it possible to bypass the adsorption and/or absorption filter. This solution, however, is technically advanced which increases the risk of technical hitches, takes up a great deal of space and is relatively expensive.

U.S. Pat. No. 6,488,028 discloses an anesthetic device where the problem regarding interruption of the anesthetic supply is solved by a rotatable filter which can be rotated between two positions with the aid of a turning element on the outside of the filter housing. When arranged in the first position, the gases breathed are forced to pass through the filter in a first gas passage while the filter, when rotated to the second position, obstructs said first gas passage, forcing the gases to bypass the filter in a second gas passage between the filter and the inside of the housing. However, this solution exposes the filter to the passing gas flow and there is a high risk that a portion of anesthetic is undesirably desorbed at the filter surface, particularly if the filter is fully saturated with anesthetic agent. This makes this solution ineffective and inappropriate for many applications.

There is a desire to be able to arrange the adsorption and/or absorption filter in a way that makes the re-use of anaesthetic effective and controllable. It is further desirable to be able to cut off the supply of anaesthetic, i.e. disconnect the anaesthetic reflecting filter, in a quick and simple way, without breaking the gas flow circuit. Further, one would like to avoid cabling and technically advanced tubing and valve solutions in the patient's immediate proximity. It is also a desire to achieve a safe, inexpensive and easy to use solution compared to the prior art.

SUMMARY OF THE INVENTION

An object of the present invention is to provide a safe, inexpensive and easy to use solution for connecting and disconnecting a filter in an arbitrary gas flow system, and particularly an adsorption and/or absorption filter in an anaesthetic delivery system, without breaking the gas flow circuit.

The object is achieved according to the present invention by a filter unit having a housing, wherein a shifting element and a filter are arranged. The shifting element is movable between at least two positions whereof the shifting element arranged in the first position allows the filter to fill the gas conducting passage in a way that forces the gas to flow through the filter whereas the shifting element arranged in the second position shifts the filter in such a way that it is substantially displaced from the gas conducting passage, allowing the gas to flow through the filter unit without passing the filter. The effect can be achieved either by letting the shifting element move the entire filter package in a substantially translational movement, or by letting the shifting element compress the filter, when moved into said second position.

That is, by using the movability or compressibility of the filter, a filter in an arbitrary gas flow system can easily be connected/disconnected without breaking the gas flow circuit. For example, an adsorption and/or absorption filter in an anesthetic delivery system can easily be disconnected and hence speed up the process of rinsing the anesthetic out of the system when it is time to wake up a patient, if too high concentrations of anesthetic agent are detected in the expiratory air, or if a patient related parameter indicates that the level of anesthesia/sedation is to deep, with reduced risk for unwanted exposure to the anesthesia agent as a result.

The present invention is a small, inexpensive and easy to handle solution which allows substantially any type of filter to be easily connected/disconnected into and out of any given gas flow system, without breaking the gas flow circuit.

In the first, second and third embodiments, summarized below, the compressibility of the filter is used to disconnect the filter. Therefore, the shifting element, causing the compression of the filter, will be called compressing element throughout the description of these embodiments. In the fourth embodiment, however, the filter package is disconnected by a substantially translational movement. Therefore, the shifting element, causing the movement, will be called translating element when describing this embodiment.

In a first embodiment of the present invention, the compressing element consists of a flexible rigid material, arranged inside the housing in such a way that it can snap between the first and the second position when exposed to an external force. In order to expose the compressing element to the external force, the housing consists at least partially of an elastic rebounding material. The cross-section of the housing walls, through a plane perpendicular to the gas flow through the filter unit, has preferably the shape of a rectangle with plane short sides and outwardly convex long sides. One advantage with the first embodiment is that the filter unit can be made very small since the entire filter unit does not have to be substantially larger than the actual filter. Another advantage is that the first embodiment does not comprise any movable parts, except for the snapable compressing element, which reduces the risk of technical hitches.

In a second embodiment of the present invention, the compressing element consists of a rigid material and the housing has a hole in the wall through which a pressing device, attached to the compressing element, is extending. The pressing device can be pushed and/or pulled in order to move the compressing element between the first and the second position.

In a third embodiment of the present invention, the housing has an opening and the compressing element is shaped in such a way that it fits tight into this opening. The compressing element has an air channel penetrating the compressing element from side to side in parallel with the gas flow through the filter unit, and is arranged in such a way that it can be pushed and pulled between the first and the second position. When arranged in the second position, the air channel is connecting the two tube-connectors which further prevents that anesthetic is desorbed from the filter. Another advantage with the third embodiment is that filter replacement is easily performed.

In a fourth embodiment, the filter is not disconnected by using the compressibility of the filter material but by simply moving the filter package aside in a substantially translational movement. This embodiment has the drawback of requiring larger filter housing than the others, but on the other hand it allows the filter to be made out of non-compressible material.

DESCRIPTION OF THE PREFERRED EMBODIMENTS

Figure 1:
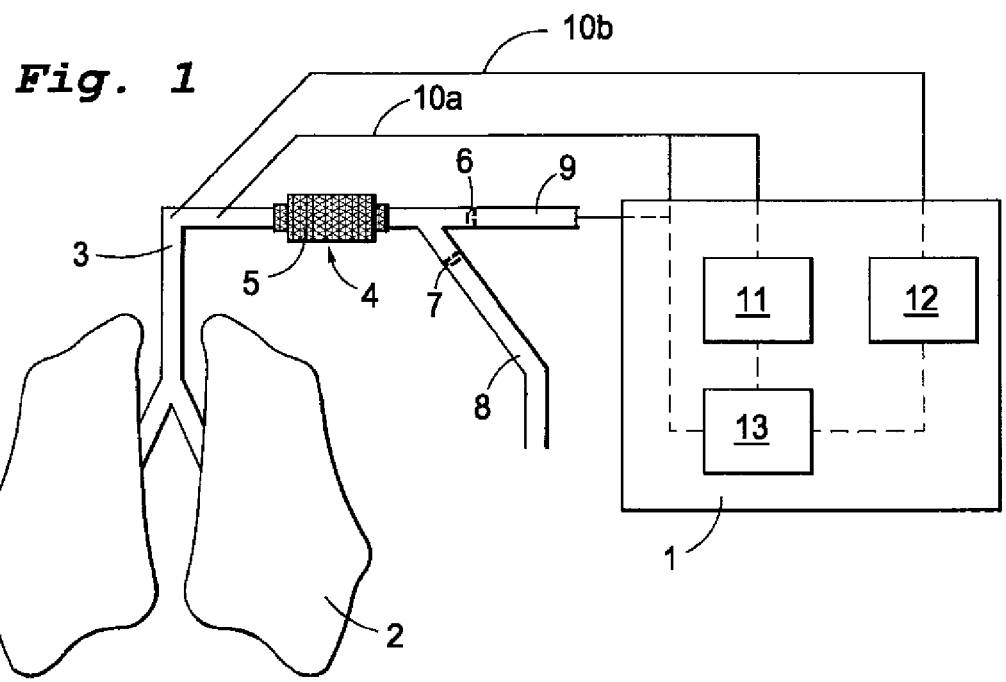
FIG. 1 is a schematic diagram of an apparatus for delivering anesthetic.

A simplified drawing of a conventional anesthetic apparatus is shown in FIG. 1. The apparatus includes a ventilator 1 that is connected to a patient 2 via a tube system, ending up in a common conduit 3 for the delivery and discharge of anesthetic and respiration gases to and from the patient 2. A filter unit 4, including a filter 5 with adsorbing and/or absorbing abilities for the adsorption and/or absorption and subsequent desorption of the anesthetics, as will be discussed below, is arranged in the common conduit 3. The design of the tube system between the patient 2 and the ventilator 1 may differ between different anesthetic apparatus but, typically, they include one-way valves 6 and 7 arranged in a Y-coupling, with one branch 8 leading to an evacuation system (not shown) for the exhalation gas, and the other branch 9 being connected to the ventilator 1 for the delivery of respiration gas. The functionality of the ventilator 1 may also differ between different anesthetic apparatus, but typically, a line 10a for the delivery of anesthetic gases from an anesthetic gasifier 11 is connected to the common conduit 3 between the patient and the adsorption/absorption filter. Further, the ventilator typically has a sample conduit 10b connected to the measuring stage 12 and a control mechanism 13 which, when connected in accordance with FIG. 1, controls the delivery of anesthetic or respiration gases so that a desired gas concentration is supplied to the patient 2.

In an exhalation phase, the exhaled gas from the patient 2 passes the filter unit 4 where the anesthetic that was not assimilated by the patient 2 in an earlier inhalation phase is adsorbed and/or absorbed by the filter 5. The majority portion of the exhalation gas, however, passes through the filter 5, through the one-way valve 7, and is evacuated from the system via the branch 8. During inhalation, fresh respiration gas is supplied to the patient 2 by the ventilator via the branch 9, the one-way valve 6, the filter unit 4 and the common conduit 3. When the fresh respiration gas passes the filter unit 4, the anesthetic that was adsorbed and/or absorbed by the filter 5 in the former exhalation phase, is desorbed and re-supplied to the patient 2. The adsorption and/or absorption material of the filter 5 should have the properties of preferring anesthetic to water and carbon dioxide. Examples of such materials are inorganic silicon aluminum compounds, zeolites, active carbon, silicone plastics, silicone oil on a porous carrier, silica gels, highly porous plastic materials, microporous silicates, etc.

The design of an anesthetic or sedation delivery system may vary somewhat and the present invention is of course intended to be used also in systems looking different than the generalized system illustrated in FIG. 1. For example, the present invention may advantageously replace the adsorption filter in the apparatus showed in FIG. 1 in U.S. Pat. No. 5,471,979. Other examples of apparatus in which the present invention may be utilized directly or after small modifications are illustrated in FIG. 3 in WO05049124 and in FIG. 2 in U.S. Pat. No. 6,286,505.

As mentioned above, the term shifting element will be replaced by either compressing element or translating element in the descriptions of the different embodiments below, depending on how the filter is displaced in each embodiment.

The First Embodiment

Figure 2A:
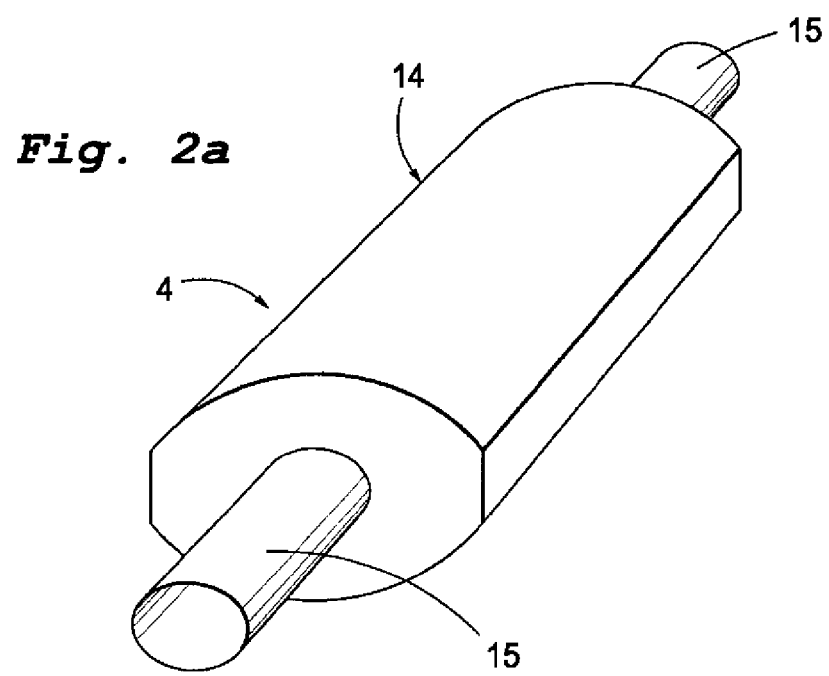
FIG. 2a is a drawing showing the housing of the first embodiment of the present invention.
Figure 2H:
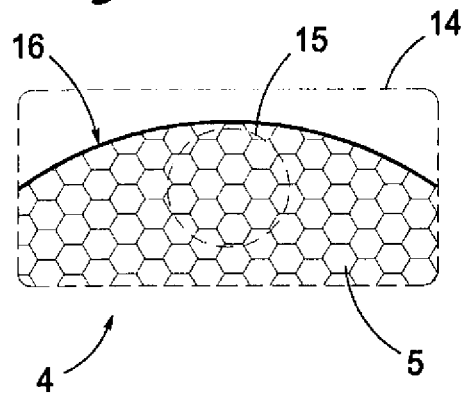
FIGS. 2h, 2k are schematic views of a cross section, through a plane perpendicular to the gas flow through the filter unit, of alternative designs of the first embodiment, showing the compressing element arranged in the first and second position, respectively.
Figure 2I:
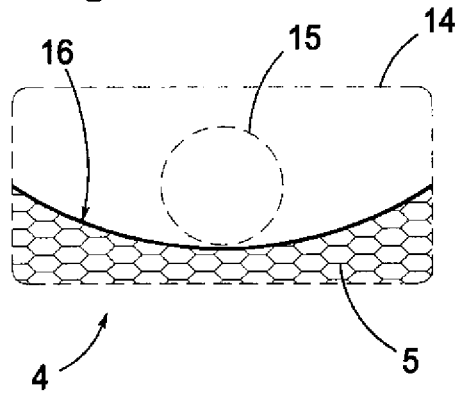
FIGS. 2b, 2c are schematic views of a first embodiment of the present invention, showing the compressing element arranged in the first and second positions, respectively.
FIGS. 2d, 2e show different designs of the compressing element in the first embodiment of the present invention.
FIGS. 2f, 2g are schematic views of a cross section, through a plane perpendicular to the gas flow through the filter unit, of the preferred design of the first embodiment, showing the compressing element arranged in the first and second position, respectively.
Figure 2J:
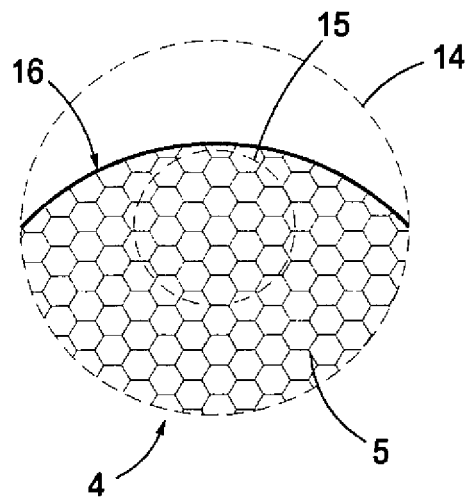
Figure 2K:
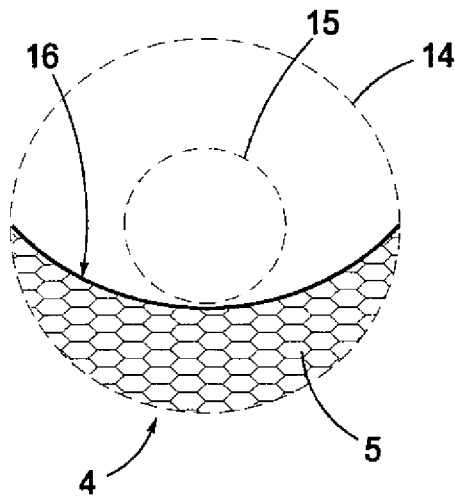

FIGS. 2a-2h illustrates the first embodiment of the present invention. In FIG. 2a, a filter unit 4 comprising a filter 5 mounted inside a housing 14 with two tube connectors 15 for easy mounting and dismounting into and out of any given gas flow system, is shown. In the preferred design of the first embodiment, the cross section of the filter unit 4, through a plane perpendicular to the gas flow through the filter unit 4, has the shape of a rectangle with plane short sides 19, connected at joints 18 to outwardly convex long sides 17, as shown in FIGS. 2f-2g. In FIGS. 2b and 2f, wherein the interior of the housing 14 is illustrated, a compressing element 16 is shown, running in parallel alongside one of the outwardly convex walls 17 of the housing 14 between said wall 17 and the filter 5. The compressing element 16 is attached to the housing 14, fixed in the joints 18 between the outwardly convex wall 17 and the plane walls 19 of the housing 14. The compressing element 16 is constructed of a rigid flexible material and arranged in such a way that it can snap from a first position, illustrated in FIGS. 2b and 2f, to a second position, shown in FIGS. 2c and 2g, and vice versa, when exposed to an external force. When the compressing element 16 is arranged in the first position (FIGS. 2b and 2f), the breathing gas flows through the filter 5 and the filter operates as the anesthetic reflector described above (the filter unit 4 is in active mode). However, when the compressing element 16 is arranged in the second position (FIGS. 2c and 2g), the filter 5 is compressed by the compressing element 16 and is substantially disconnected from the gas flow circuit, allowing breathing gas to flow through the housing 14 without the reflection of anesthetic taking place (the filter unit 4 is in passive mode).

One of the reasons why the filter unit 4 has a substantially elliptical cross section as described above, is that the compressing element 16, arranged in the first position, will follow alongside one of the outwardly convex walls 17, allowing the filter 5 to fill the entire interior of the housing 14 and thus force the respiration gas to pass through the full length of the filter 5. Another advantage with this filter unit geometry is that the filter unit 4 can be made very small since the entire filter unit 4 does not have to be substantially larger than the actual filter 5. This eliminates unnecessary dead space from the tubing system. However, the principle with the snapable compressing element 16, described in the first embodiment of the present invention, is applicable to filter units having any given geometrical shape. Further variations of the first embodiment are, for example, filter units having a cross section, through a plane perpendicular to the gas flow through the filter unit, shaped as a rectangle or a circle as showed in FIGS. 2h-2k. However, the suggested varieties have the drawback of increasing the volume in the tubing system, thus increasing the system dead space.

The compressing element 16 in the first embodiment may be made of any rigid and flexible material, such as metal, wood, plastic, vinyl or any polymer derived material. Further, the compressing element 16 may be formed wholly or partially of the rigid flexible material, i.e. it may have a net or perforated sheet structure, it may be built up by just one or several ribs 20 (as shown in FIG. 2d) or it may be a solid body without any cavities (in accordance to FIG. 2b-2c). The compressing element 16 may also be composed by several component parts, for example, an elastic plastic or fabric sheet 21 may be arranged between one or several flexible ribs 20 and the filter 5 in accordance to FIG. 2e. Preferably, the compressing element 16 is formed of a gas-tight material which shields the filter 5 from the gas and therefore prevents that anesthetic is desorbed at the filter surface when the filter 5 is compressed. This is particularly important if the filter is fully saturated with anesthetic agent and the gas flow through the filter unit 4 is low.

To be able to expose the compressing element 16 to an external force in order to make it snap from one position to the other, the housing 14, and particularly the outwardly convex walls 17, should be formed at least partially of an elastic rebounding material, preferably a type of plastic.

The Second Embodiment

Figure 3A:
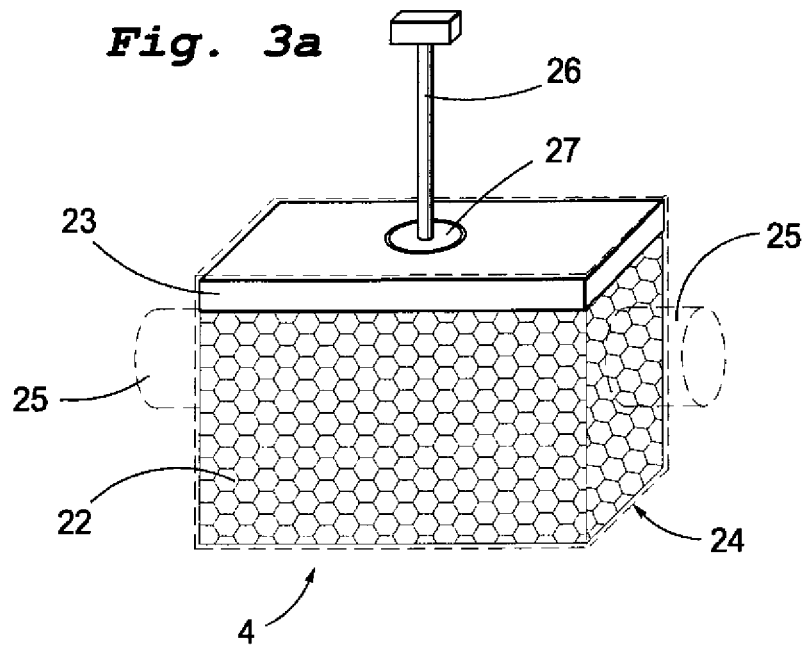
FIGS. 3a, 3b are schematic views of a second embodiment of the present invention, showing the compressing element arranged in the first and second position, respectively.
Figure 3B:
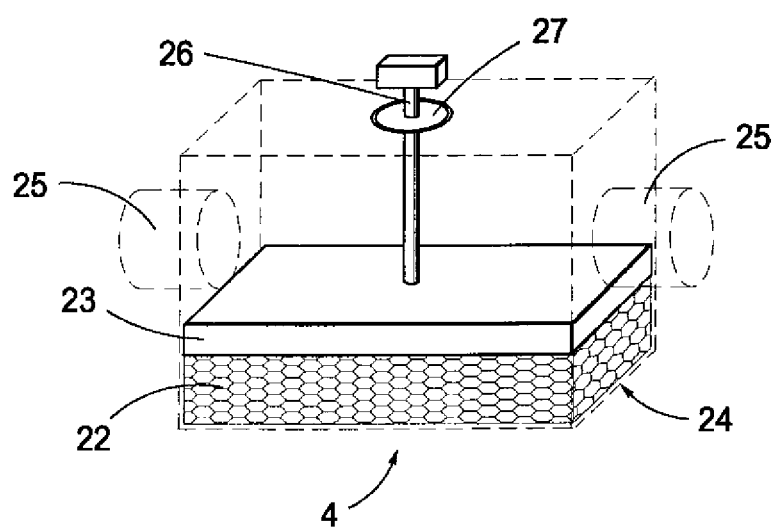

A second embodiment of the present invention is illustrated in FIGS. 3a-3b wherein a filter unit 4 having a filter 22 and a compressing element 23, enclosed in a housing 24 with two tube-connectors 25, is shown. Furthermore, the housing 24 has a hole in the wall through which a pressing device 26, attached to the compressing element 23 is extending. The pressing device 26 consists of a rigid material and can be pushed and/or pulled in order to move the compressing element 23 between a first and at least a second position. The housing 24 further has a hermetically sealing elastic membrane 27, arranged in the hole in the housing around the pressing device 26, in order to stop potential leakage of gas between the hole and the pressing device 26. A further alternative to prevent the leakage of anesthetic agents to the surrounding air is to enclose the pressing device 26 in a bellows.

When the compressing element 23 is arranged in the first position, shown in FIG. 3a, the breathing gas flows through the filter 22 and the anesthetics is therefore reflected, i.e. the filter unit 4 is in active mode. Referring now to FIG. 3b, the filter unit 4 is deactivated by simply pressing the pressing device 26, forcing the compressing element 23 to compress the filter 22 in a way that enables the breathing gas to flow through the filter unit 4 without passing the filter 22. After pressing the pressing device 26, a locking device (not shown) may be used to ensure that the compressing element 23 stays in the second position although exposed to a force from the substantially compressed filter 22. However, the need for such a locking device can be eliminated by arranging friction means on the compressing element 23 and/or the interior walls of the housing 24 so that the friction between the compressing element 23 and the walls of the housing 20 is sufficient high to hold the compressing element 23 in any given position. Yet another alternative is to arrange the elastic membrane 27 to fit sufficiently tight to the pressing device 26 so as to obtain the friction needed to hold the compressing element 23 in a given position.

It is normally desirable that the compressing element 23 has the same shape and area as the cross section of the housing 24 through a plane, parallel with the gas flow streaming through the filter unit, in order to fit tight into the housing 24 and hence be able to substantially disconnect the filter 5 from the gas flow system when moved into the second position, as showed in FIG. 3b. However, it is possible to substantially disconnect the filter 22 even though the compressing element 23 does not fit tight into the housing 24 and therefore, it should be envisioned that the second embodiment of the present invention is applicable to filter units with any given geometry.

The Third Embodiment

Figure 4A:
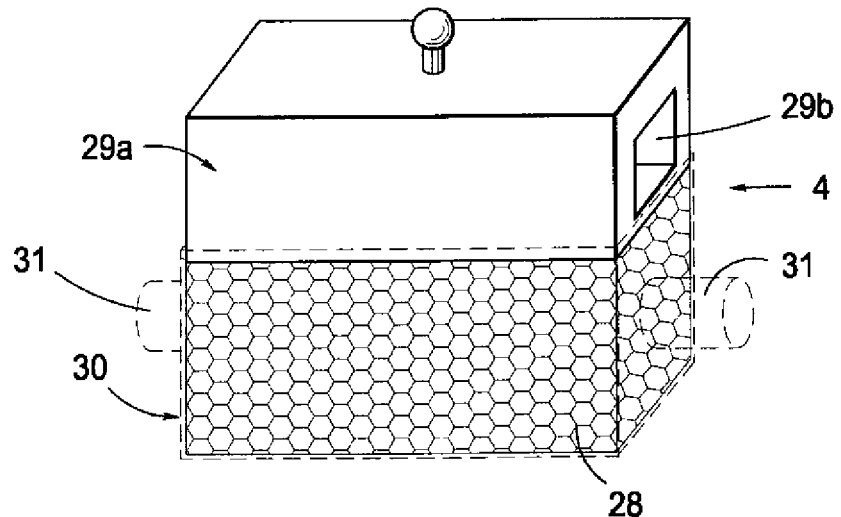
FIG. 4a, 4b are schematic views of a third embodiment of the present invention, showing the compressing element arranged in the first and second position, respectively.
Figure 4B:
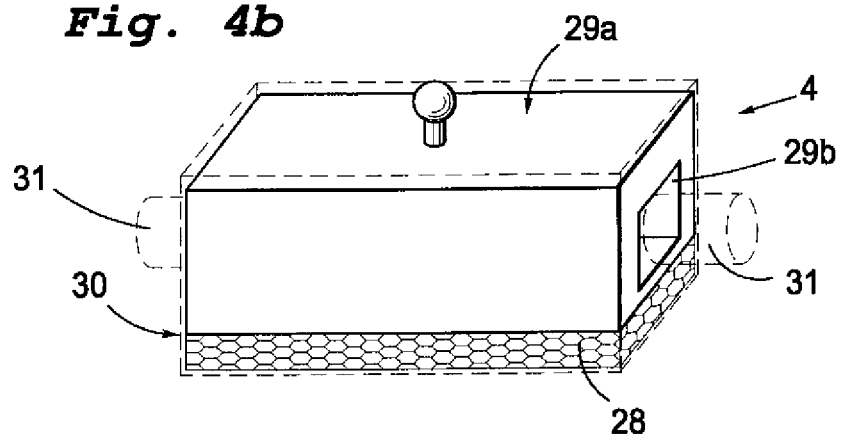

A third embodiment of the present invention is illustrated in FIGS. 4a-4b, wherein a filter unit 4, comprising a filter 28 and a compressing element 29a, partially mounted inside a housing 30 with two tube connectors 31, is shown. In this embodiment, the housing 30 has an opening and the compressing element 29a is shaped in such a way that it fits tight into this opening. An air channel 29b is penetrating the compressing element 29a from side to side, in parallel with the direction of the gas flow through the filter unit 4.

When the compressing element 29a is arranged in the first position, shown in FIG. 4a, the compressing element 29a prevents the breathing gas from leaking out of the filter unit 4, forcing the breathing gas to flow through the filter 28, i.e. the filter unit 4 is in active mode. The filter unit 4 is deactivated by simply pushing the compressing element 29a into the second position, illustrated in FIG. 4b, wherein the filter 28 is compressed and the air channel 29b of the compressing element 29a connects the two tube-connector 31 openings in such a way that the breathing gas can flow through the filter unit 4 without passing the filter 28.

Yet another design of the third embodiment (not shown) includes a larger housing that fully encloses the compressing element 29a. To be able to displace the compressing element 29a inside the housing and to minimize the size of the filter unit when in passive mode, the part of the housing that surrounds the compressing element 29a when the filter unit is in active mode, may be contractible. This feature can be obtained by, for example, letting this part of the housing be accordion-folded.

Although the illustrated filter unit in FIGS. 4a-4b has the shape of a rectangular block, it should be envisioned that the third embodiment of the present invention applies to filter units with many different geometrical shapes.

The Fourth Embodiment

Figure 6A:
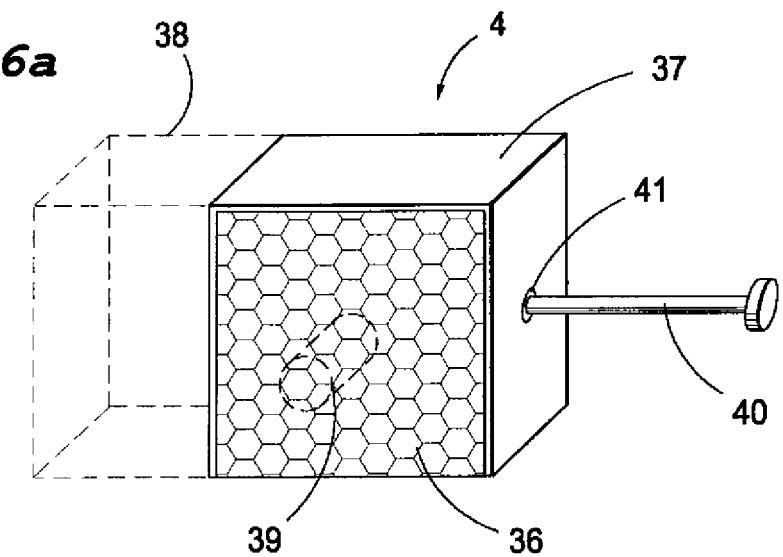
FIGS. 6a, 6b are schematic views of a fourth embodiment of the present invention, showing the translating element arranged in the first and second position, respectively.
Figure 6B:
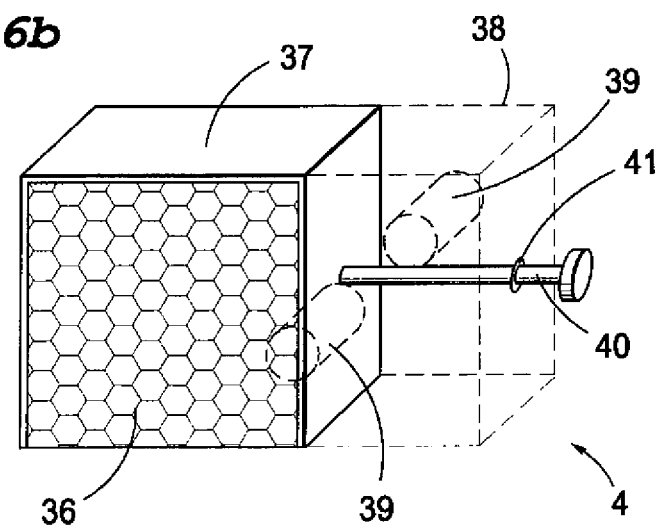

A fourth embodiment of the present invention is illustrated in FIGS. 6a-6b wherein a filter unit 4 comprising a filter 36 and a translating element 37, enclosed in a housing 38 with two tube-connectors 39, is shown. Furthermore, the housing 38 has a hole in the wall through which a pressing device 40, attached to the translating element 37 is extending. The pressing device 40 is formed of rigid material and can be pushed and/or pulled in order to move the translating element 37 between a first and at least a second position. The housing 38 further has a hermetically sealing elastic membrane 41, arranged in the hole in the housing around the pressing device 40, in order to stop potential leakage of gas between the hole and the pressing device 40. A further alternative to prevent the leakage of anesthetic agents to the surrounding air is to enclose the pressing device 40 in a bellows.

When the translating element 37 is arranged in the first position, shown in FIG. 6a, the breathing gas flows through the filter 36 and the anesthetics is therefore reflected, i.e. the filter unit 4 is in active mode. The filter unit 4 is deactivated by simply pressing the pressing device 40 which causes the translating element 37 to move the filter 36 in a substantially translational movement, into the position showed in FIG. 6b, enabling the breathing gas to flow through the filter unit 4 without passing the filter 36. Just like in the second embodiment described above, locking devices (not shown) or friction means arranged on the translating element 37 and/or the interior walls of the housing 38 may be used to ensure that the translating element 37 stays in the desired positions.

In order to make the filter unit 4 smaller, the part of the housing 38 that is not occupied by the filter 36 and the translating element 37 when the filter unit 4 is in active mode (see FIG. 6a), may be contractible. This feature can be obtained by, for example, letting said part of the housing 38 be accordion-folded (not shown).

The translating element 37 illustrated in FIGS. 6a-6b has the shape of a rectangle where one of the four walls is left out to facilitate filter replacement. The translating element 37 may, however, have any possible shape but it should preferably surround the filter 36 sufficiently much to make it possible to move the filter 36 in both directions when pressing/pulling the pressing device 40. Further, the housing 38 needs to be large enough to allow the filter 36 to be moved to an extent where the gas can flow through the filter unit 4 without passing through the filter 36. Although FIGS. 6a-6b illustrates a rectangular shaped filter unit 4 it should be envisioned that not only the translating element 37 but also the housing 38, the filter 36 and the pressing device 40, could have different shapes.

Figure 5A:
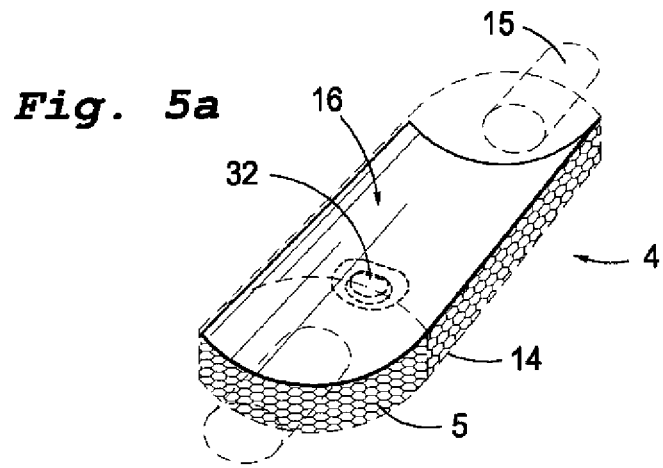
FIGS. 5a, 5c are drawings showing the housing of the different embodiments, comprising a one-way valve.
Figure 5B:
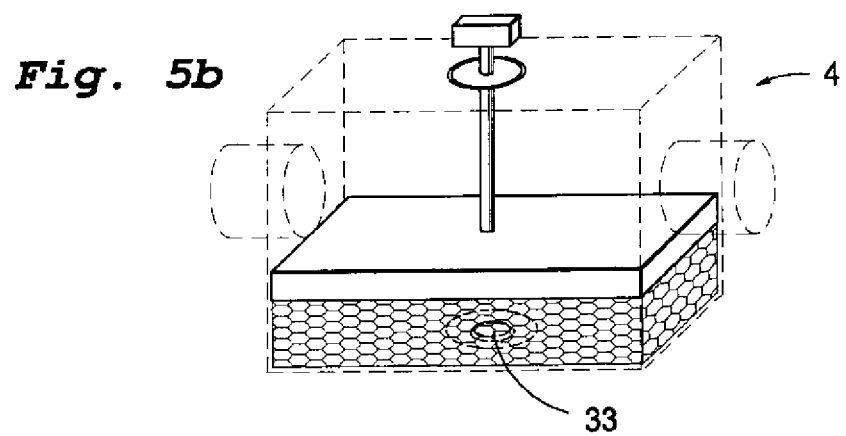
Figure 5C:
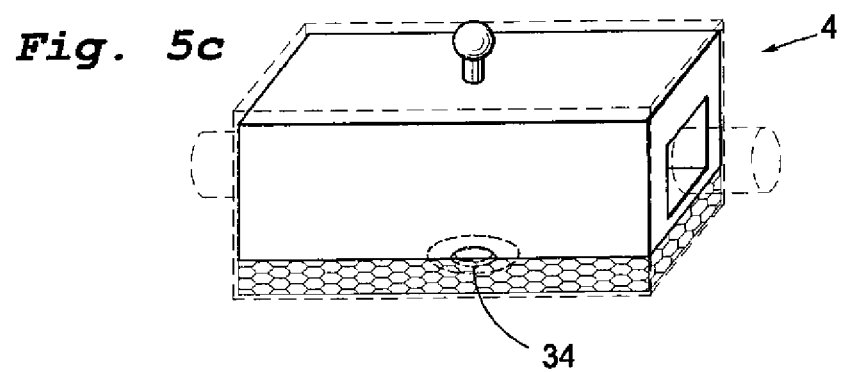

General Characteristics the shifting elements 16, 23, 29a, 37 in the different embodiments may or may not be made out of airtight material. If the material in the compressing element 16, 23, 29a is airtight (and the joints between the compressing element 16, 23, 29a and the housing 14, 24, 30 are also airtight), the gas, currently bounded in the filter 5, 22, 28 will have no where to go when the filter is compressed. Thus, the compressing element 16, 23, 29a will not be able to compress the filter unless the bounded gas can leave the system. Therefore, a one-way valve 32, 33, 34 may be built into the filter unit housing 14, 24, 30 in accordance to FIG. 5a-5c, allowing the gas to exit the housings 14, 24, 30 when the filters 5, 22, 28 are compressed. The one-way valve 32, 33, 34 is preferably connected to a so called scavenging system (not shown) in order to reduce the exposure of operating room personnel to waste anesthetic agents vented from the breathing system.

The filter unit 4 may be arranged in any possible direction but the first, second and third embodiment of the present invention is preferably arranged in such a way that the filter 5, 22, 28 is compressed downwards (as in the figures) when disconnected. Arranged in this way, (fluid) anesthetic is prevented from leaking into the housing 14, 24, 30 and re-enter the gas flow system when the filter 5, 22, 28 is compressed, in case the compressing element 16, 23, 29a is not waterproof and/or airtight.

Regarding the position of the filter unit 4 in the anesthetic apparatus (see FIG. 1), there is a desire to arrange the adsorption and/or absorption filter in a way that makes the re-use of anesthetic effective and controllable. It is further desirable to shorten the distance between the filter unit and the Y-coupling as much as possible in order to prevent exhaled carbon dioxide to be re-inhaled during the inhalation phase. However, the filter unit may be placed anywhere within the exhalation branch in the tube system between the patient 2 and the ventilator 1.

Moving the shifting element 16, 23, 29a, 37 between the first and the second position, i.e. connecting/disconnecting the filter 5, 22, 28, 36, is preferably accomplished manually by simply squeezing the filter housing 14 in the first embodiment, pressing or pulling the pressing device 26 in the second and fourth embodiments and pushing and pulling the compressing element 29a in the third embodiment, respectively. One obvious advantage with the present invention is that the connection/disconnection of the filter can be accomplished with only one hand. However, the change of state may also be accomplished electromechanically. As mentioned in the background of the invention, it is desirable to cut off the supply of anesthetic quickly if, e.g., some patient related parameter indicates that the level of anesthesia/sedation is too deep. Examples of such parameters are pulse, blood pressure and level of spontaneous respiratory drive etc., well known to a person skilled in the art. By having sensors monitoring one or several of these parameters and letting a control mechanism act upon the sensor signals, it is possible to automatically connect/disconnect the filter 5, 22, 28, 36 when a parameter deviates from what is considered as normal.

Upon delivery, the filter unit 4 may be in passive mode or active mode, i.e. the shifting element 16, 23, 29a, 37 may be in either the first or the second position. Further, the filter unit 4 may be preloaded with the anesthetic agent or may have an injection membrane for adding the anesthetic agent at a later stage, as is known from WO03/090826, which is particularly desirable if the filter unit 4 is included in hand-driven respiration devices in field systems used, e.g., in field hospitals or by veterinaries. To prevent the filter 5, 22, 28, 36 from getting in contact with air or other gases before the actual time of application, it may be desirable to arrange the filter 5, 22, 28, 36 in the second position and even to conceal the two tube-connectors 15, 25, 31, 39 with a suitable shielding medium such as a cap or a rip off seal upon manufacturing. This is particularly relevant if the filter unit is delivered preloaded with a sedation or anesthesia agent.

For a cost-efficient usage of the filter unit 4, a used filter 5, 22, 28, 39 can be replaced by a new one. In order to change filter 5, 22, 28, 36 the housings 14, 24, 38 may be openable in the first, second and fourth embodiment of the present invention and the shifting element 29a in the third embodiment may be arranged so that it can be lifted out of the housing 30. The filter unit 4 can hence be designed to be either disposable or non-disposable. It can further be autoclavable or in other ways sterilizable in order to be reused in a hygienic way.

Although the described embodiments show a displacement of the filter that is substantially perpendicular to the direction of the gas flow, the filter displacement can of course be performed at a different angle to the gas flow direction if the filter housing is designed accordingly, without diverting from the inventive concept of the present invention.

While the present invention has been described with reference to gas flow circuits in anesthetic apparatus, this description is not intended to be construed in a limiting sense The filter unit 4 according to the present invention may be arranged in any given gas flow system where there is a need for connecting and disconnecting any kind of filter in a quickly and smooth manner Other application areas where the invention would be suitable are, for example, in filter systems for gas masks and in portable anesthetic devices for use in field hospitals and emergency care.

Although modifications and changes may be suggested by those skilled in the art, it is the intention of the inventor to embody within the patent warranted heron all changes and modifications as reasonably and properly come within the scope of his contribution to the art.

I claim as my invention:

1. A filter unit comprising:
    a filter housing;
    said filter housing having an inner volume and first and second gas connectors respectively configured for connecting said filter housing to a gas conducting passage, said first and second gas connectors communicating with said inner volume and defining a portion of said gas conducting passage that proceeds through said inner volume of said filter housing;
    a filter in said inner volume of said filter housing, said filter being selected from the group consisting of adsorption filters and absorption filters, said filter consisting of a compressible filter material;
    a compressing element mounted in said filter housing for movement between a first position and a second position in said inner volume upon exposure to an external force;
    said compressing element, in said first position, causing said filter material and said compressing element to occupy and entirely fill said inner volume of said filter housing to substantially fill said portion of said gas conducting passage in said inner volume of said filter housing to force gas in said gas conducting passage to pass through said filter material; and
    said compressing element, in said second position, compressing said filter material to substantially displace said filter material into, and maintain said filter material in a compressed state that is entirely within said inner volume of said filter housing, said filter material in said compressed state causing gas in said gas conducting passage to proceed through said filter housing without interacting with said filter material.

2. A filter unit as claimed in claim 1 wherein said compressing element is mounted in said filter housing to prevent any gas passing through the filter housing from coming into contact with said filter material when said compressing element is in said second position.

3. A filter unit as claimed in claim 2 wherein said compressing element is comprised of flexible material and snaps between said first and second positions upon exposure to said external force.

4. A filter unit as claimed in claim 3 wherein said filter housing comprises a housing part comprised of elastically rebounding material that exposes the compressing element inside the filter housing to said external force, by application of external pressure to said housing part.

5. A filter unit as claimed in claim 3 wherein said filter housing comprises housing walls having a cross-section, through a plane perpendicular to gas flow through the filter housing, with plane short sides connected at joints to outwardly convex long sides, said compression element being fixed in said joints between one of the outwardly convex sides and the two plane short sides, bending toward and running parallel along said outwardly convex side when in said first position, and bending in an opposite direction, parallel with the other outwardly convex side, with the filter material compressed between the filter housing and the other convex side, when in said second position.

6. A filter unit as claimed in claim 1 wherein said filter housing has a wall with a hole therethrough, and comprising a pressing element connected to said compressing element and extending through said hole, said pressing element being actuatable in order to move said compressing element between said first position and said second position.

7. A filter unit as claimed in claim 6 wherein said compressing element has a same shape and area as a cross-section of said filter housing through a plane that is parallel with flow of said gas to said filter housing.

8. A filer unit as claimed in claim 1 wherein said filter housing has an opening in which said compressing element is tightly fit, said compressing element having an air channel penetrating said compression element from one side thereof to another parallel with flow of gas to said filter housing, said air channel also being movable between said first and second positions, with said compressing element, in said first position, covering said opening in said housing wall to prevent gas from leaking out while allowing said filter material to substantially fill said portion of said gas conducting passage in said filter housing to force gas to flow through the filter material, and said compressing element, in said second position, compressing said filter material and the air channel of the compressing element engaging the first and second connectors to allow gas to flow through the filter housing without interacting with said filter material.

9. A filter unit as claimed in claim 8 wherein said compressing element is removably mounted in said filter housing to allow exchange of said filter material from said filter housing.

10. A filter unit as claimed in claim 1 wherein said filter housing comprises a one-way valve positioned to allow gas bounded in said filter material to exit said filter housing when said compressing element is moved into said second position and the filter material is compressed.

11. A filter unit as claimed in claim 10 wherein said one-way valve is connected to a scavenging system.

12. A filter unit as claimed in claim 1 wherein said filter housing has a wall with a hole therethrough, and wherein said compressing element has a pressing device attached thereto that extends through said hole that is actuatable to move said compressing element between said first and second positions, and further comprising a hermetically sealing elastic membrane in said hole surrounding said pressing element, that precludes leakage of gas between the housing wall and the pressing element.

13. A filter unit as claimed in claim 1 wherein said filter housing has a wall with a hole therethrough, and wherein said compressing element has a pressing element attached thereto that extends through said hole, said pressing element being actuatable to move said compressing element between said first and second positions, and further comprising frictional material between said hole and said pressing element that allows said pressing element to be held in any position relative to said wall of said housing.

14. A filter unit as claimed in claim 1 wherein said housing has a wall with a hole therein, and wherein said compressing element has a pressing element attached thereto that extends through said hole, said pressing element being actuatable to move said compressing element between said first and second positions, and further comprising a locking device that locks said pressing element in either of said first position or said second position.

15. A filter unit as claimed in claim 1 wherein said housing has an openable portion that allows access to said filter material to allow exchange of said filter material from said filter housing.

16. A filter unit as claimed in claim 1 wherein said compressing element comprises a solid body having no cavities therein.

17. A filter unit as claimed in claim 1 wherein said compressing element has at least one rib.

18. A filter unit as claimed in claim 17 comprising an elastic plastic or fabric sheet between said rib and said filter material.

19. A filter unit as claimed in claim 1 wherein said compressing element comprises a non-solid body having a net-like structure.

20. A filter unit as claimed in claim 19 comprising an elastic plastic or fabric sheet between said non-solid body and said filter material.

21. A filter unit as claimed in claim 1 wherein said compressing element consists of airtight material.

22. A filter unit as claimed in claim 1 wherein said compressing element is manually movable between said first and second positions.

23. A filter unit as claimed in claim 1 wherein said compressing element is electromechanically movable between said first and second positions.

\* \* \* \* \*